United States Patent [19]

Halbritter

[11] 4,302,584
[45] Nov. 24, 1981

[54] PREPARATION OF 3,3-DIMETHYL-PENT-4-ENOIC ACID AMIDES

[75] Inventor: Klaus Halbritter, Mannheim, Fed. Rep. of Germany

[73] Assignee: BASF Aktiengesellschaft, Fed. Rep. of Germany

[21] Appl. No.: 175,939

[22] Filed: Aug. 7, 1980

[30] Foreign Application Priority Data

Sep. 19, 1979 [DE] Fed. Rep. of Germany ....... 2937815

[51] Int. Cl.³ .................. C07C 102/00; C07D 295/10
[52] U.S. Cl. .............................. 544/176; 260/326 SE; 546/245; 564/204; 564/205
[58] Field of Search ............................. 564/204, 205; 260/326 SE; 544/176; 546/245

[56] References Cited

FOREIGN PATENT DOCUMENTS 2732213  1/1979  Fed. Rep. of Germany .
52-83411 7/1977  Japan .

OTHER PUBLICATIONS

Felix et al., Helv. Chim. Acta 52, (1969), pp. 1030–1034.
Wick et al., Helv. Chim. Acta 47, (1964), pp. 2425–2429.
Roux et al., Con. J. Chem. 47, (1969), pp. 4455–4458.

Bredereck et al., Chem. Bericht. 96, (1963), pp. 1350–1355.
Meerwein et al., Annalen 641, (1961), pp. 1–39.

*Primary Examiner*—Arthur P. Demers
*Attorney, Agent, or Firm*—Keil & Witherspoon

[57] ABSTRACT

A process for the preparation of 3,3-dimethyl-pent-3-enoic acid amides of the formula I

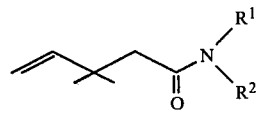

where $R^1$ and $R^2$ may be identical or different and each is alkyl of 1 to 4 carbon atoms, or $R^1$ and $R^2$ together with the nitrogen on which they are present as substituents form a 5-membered or 6-membered saturated ring which may contain a further hetero-atom, wherein an acetamido-acetal or ketene-acetal-aminal is reacted with 3-methyl-but-2-en-1-ol at from 80° to 220° C., in the presence or absence of an inert organic solvent. The products are valuable intermediates for the preparation of insecticidal cyclopropanecarboxylic acid esters.

4 Claims, No Drawings

PREPARATION OF 3,3-DIMETHYL-PENT-4-ENOIC ACID AMIDES

The present invention relates to a process for the preparation of 3,3-dimethyl-pent-4-enoic acid amides by reacting an acetamido-acetal or ketene-acetal with 3-methyl-but-2-en-1-ol.

The preparation of 3,3-dimethyl-pent-4-enoic acid amides by reacting 3,3-dimethyl-acrylamides with acetaldehyde in the presence of a peroxide, to give 3,3-dimethyl-3-acetyl-acetamides, which are then reduced and dehydrated is disclosed in Japanese Laid-Open Application 77/83,411. Furthermore, 3,3-dimethyl-pent-4-enoic acid amides may be prepared in a conventional manner from 4-cyano-3,3-dimethyl-but-1-ene or 3,3-dimethyl-pen-4-enoic acid (German Laid-Open Application DOS No. 2,732,213).

I have found that a 3,3-dimethyl-pent-4-enoic acid amide of the formula I

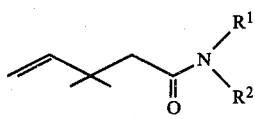   I where $R^1$ and $R^2$ may be identical or different and each is alkyl of 1 to 4 carbon atoms, or $R^1$ and $R^2$ together with the nitrogen on which they are present as substituents form a 5-membered or 6-membered saturated ring which may contain a further hetero-atom, are obtained in an advantageous manner by a reaction wherein an acetamido-acetal of the formula II

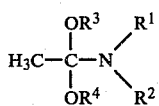   II where $R^3$ and $R^4$ may be identical or different and each is alkyl of 1 to 4 carbon atoms, or $R^3$ and $R^4$ together are unbranched or branched alkylene of 2 or 3 carbon atoms, and $R^1$ and $R^2$ have the above meanings, or a ketene-acetal-aminal of the formula III

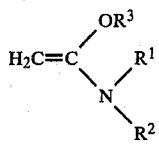   III where $R^3$ is alkyl of 1 to 4 carbon atoms and $R^1$ and $R^2$ have the above meanings, is reacted with 3-methyl-but-2-en-1-ol at from 80° to 200° C.

The reaction of an acetamido-acetal or ketene-acetal-aminal with an allyl alcohol is known in principle. However, if the allyl alcohol is 3,3-dialkyl-substituted, as in the case of geraniol, it is necessary to heat the components for several hours at 150° C. (Helv. Chim. Acta 47 (1964), 2425–2429, and ibid. 52 (1969), 1031).

Since, however, it is to be expected that 3-methyl-but-2-en-1-ol, which is unstable at elevated temperatures, would undergo dehydration at 140° C. and become converted to dienes, oligomers and polymers or undergo rearrangement to 3-methyl-but-3-en-1-ol, a compound which cannot be used in the novel process (Canad. J. Chem. 47 (1969), 4455–4458), it was in no way to be expected that the reaction of 3-methyl-but-2-en-1-ol with an acetamidoacetal or ketene-acetal-aminal at an elevated temperature would take place without the formation of by-products and with excellent yields.

Using the process according to the invention, it is possible to prepare 3,3-dimethyl-pent-4-enoic acid amides of the formula I, where $R^1$ and $R^2$ are identical or different and are unbranched or branched alkyl of 1 to 4 carbon atoms, eg. methyl, ethyl, n-propyl, i-propyl or butyl. Furthermore, $R^1$ and $R^2$, together with the nitrogen on which they are present as substituents, can form a 5-membered or 6-membered saturated ring which may contain a further hetero-atom; examples of such rings are pyrrolidine, piperidine and morpholine.

The acid amides of the formula I are valuable intermediates for the synthesis of insecticidally active compounds. They may be reacted with tetrahalomethanes in the presence of a catalyst to give 6,6,6,4-tetrahalo-3,3-dimethylhexanoic acid amides, which in turn can be converted to 2-(2,2-dihalovinyl)-3,3-dimethyl-cyclopropanecarboxylic acid amides by treatment with a base (German Laid-Open Application DOS No. 2,732,213).

Suitable starting materials are acetamido-acetals of the formula II, where $R^1$ and $R^2$ have the above meanings and the substituents $R^3$ and $R^4$ may be identical or different and are unbranched or branched alkyl of 1 to 4 carbon atoms, eg. methyl, ethyl, n-propyl, i-propyl or butyl. $R^3$ and $R^4$ may also together form an unbranched or branched alkylene of 2 or 3 carbon atoms, i.e., ethylene, trimethylene or propylene. Ketene-acetal-aminals suitable for use as starting materials are those compounds of the formula III, where the substituents $R^1$ and $R^2$ have the above meanings, and $R^3$ is unbranched or branched alkyl of 1 to 4 carbon atoms, eg. methyl, ethyl, n-propyl, i-propyl or butyl. Mixtures of an acetamido-acetal and a ketene-acetal-aminal may also be used, provided that $R^1$ and $R^2$ in formula II have the same meanings as in formula III.

The starting materials of the formula II or III, some of which are known, may be prepared by analogy with conventional methods (Ann. Chem. 641 (1961), 1–39; Chem. Ber. 96 (1963), 1350–1355).

The ratio in which the starting materials are used may vary within wide limits; advantageously, from 0.9 to 1.3 moles of 3-methyl-but-2-en-1-ol are employed per mole of acetamido-acetal of the formula II or ketene-acetal-aminal of the formula III or of a mixture of these.

The reaction is carried out batchwise or continuously, under atmospheric or superatmospheric pressure, at from 80° to 200° C., preferably from 130° to 160° C.

The reaction takes place smoothly and in high yields, either in the absence or in the presence of a solvent. Suitable inert organic solvents include aliphatic and aromatic hydrocarbons, eg. xylenes, mesitylene, chlorobenzene, nitrobenzene, tetralin and decalin, acyclic and cyclic ethers, eg. di-n-butyl ether, diethylene glycol diethyl ether, dioxane, tetrahydrofuran, diphenyl ether and anisole, and also tetramethylene sulfone, dimethylformamide, dimethylacetamide, tetramethylurea and benzonitrile.

To carry out the process according to the invention, the reaction mixture of 3-methyl-but-2-en-1-ol and acetamido-acetal or ketene-acetal-aminal, with or without solvent, is heated from room temperature to the desired reaction temperature, in general in the course of from 20 minutes to 3 hours. The alcohol of the formula R³OH or R⁴OH, formed in the course of this heating, by trans-acetalization or ketene-acetal-aminal formation, prior to the actual main reaction, is advantageously removed by distillation. The end product can be obtained in high purity by distillation through a short column. For further conversion, the reaction product may also be employed directly, without first being isolated by distillation.

The Examples which follow illustrate the process according to the invention.

EXAMPLE 1

147 g of 3-methyl-but-2-en-1-ol are added to 180 g of a mixture of 72.5% by weight of N,N-dimethylacetamide-dimethylacetal and 27.5% by weight of 1-dimethylamino-1-methoxyethylene, and the batch is brought to 144° C. in the course of 80 minutes, whilst at the same time distilling the resulting methanol from the reaction mixture. The batch is then heated for 100 minutes at 144°–154° C. Distillation through a short column gives 205 g (90%) of 3,3-dimethyl-pent-4-enoic acid N,N-dimethylamide (of boiling point 70° C./2.6 mbar), corresponding to a yield of 90% of theory.

| $C_9H_{17}NO(155)$ | C | H | N | O |
| --- | --- | --- | --- | --- |
| Calculated: | 69.6 | 11.0 | 9.0 | 10.3 |
| Found: | 69.3 | 10.8 | 9.1 | 10.6 |

¹H-NMR (in d₆-DMSO)
1.15 ppm (S), 6 protons),
2.30 ppm (S), 2 protons,
2.88 ppm (S), 3 protons,
2.96 ppm (S), 3 protons,
4.82 ppm (D; $J_{cis}=10$ Hz), 1 proton;
4.85 ppm (D; $J_{trans}=18$ Hz), 1 proton;
5.85 ppm (DD); $J_{cis}=10$ Hz, $J_{trans}=18$ Hz), 1 proton.

EXAMPLE 2

279.1 g of 3-methyl-but-2-en-1-ol are added to 359.7 g of a mixture containing 87.6% by weight of N,N-dimethylacetamide-dimethylacetal and 7.3% by weight of 1-dimethylamino-1-methoxyethylene, and the batch is brought to 144° C. in the course of 60 minutes, and is kept at the same temperature for a further 120 minutes. During heating, and at the final temperature, the methanol formed is distilled off directly through a short column. On subsequent distillation through a ½ meter column, 58.8 g of first runnings, containing about 7.9% by weight of 3,3-dimethyl-pent-4-enoic acid N,N-dimethylamide are obtained at 37°–55° C./0.8 mbar, followed, at 55°–62° C./0.8 mbar, by 392.3 g of 3,3-dimethyl-pent-4-enoic acid N,N-dimethylamide of purity 98.2 percent by weight. The residue, amounting to 9.8 g, contains 80.7% by weight of product, so that the total yield of 3,3-dimethyl-pent-4-enoic acid N,N-dimethylamide amounts to 97.7% of theory. (The content of 3,3-dimethyl-pent-4-enoic acid N,N-dimethylamide can be determined by gas chromatography).

I claim:

1. A process for the preparation of a 3,3-dimethyl-pent-4-enoic acid amide of the formula I

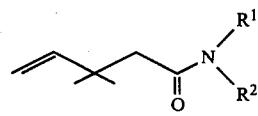

where
R¹ and R² may be identical or different and each is alkyl of 1 to 4 carbon atoms, or R¹ and R² together with the nitrogen on which they are present as substituents form a pyrrolidine, piperidine or morpholine ring,
wherein an acetamido-acetal of the formula II

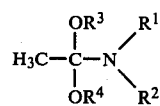

where
R³ and R⁴ may be identical or different and each is alkyl of 1 to 4 carbon atoms, or R³ and R⁴ together are unbranched or branched alkylene of 2 or 3 carbon atoms, and R¹ and R² have the above meanings,
or a ketene-acetal-aminal of the formula III

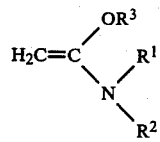

where
R³ is alkyl of 1 to 4 carbon atoms and R¹ and R² have the above meanings,
is reacted with 3-methyl-but-2-en-1-ol at from 80° to 200° C.

2. A process as claimed in claim 1, wherein 3-methyl-but-2-en-1-ol is reacted with a mixture of an acetamido-acetal of the formula II and a ketene-acetal-aminal of the formula III, R¹ and R² in formula II having the same meanings as in formula III.

3. A process as claimed in claim 1, wherein the reaction is carried out in the presence of an inert organic solvent.

4. A process as claimed in claim 1, wherein the reaction is carried out at from 130° to 160° C.

* * * * *